United States Patent [19]
Marlow

[11] Patent Number: 5,989,294
[45] Date of Patent: Nov. 23, 1999

[54] BALL-AND-SOCKET JOINT, PARTICULARLY A PROSTHETIC HIP JOINT

[76] Inventor: Aaron L. Marlow, 1346 Ambridge Way, Ottawa, Canada, K2C 3T4

[21] Appl. No.: 09/124,518

[22] Filed: Jul. 29, 1998

[51] Int. Cl.⁶ .................................................... A61F 2/34
[52] U.S. Cl. .............................................................. 623/22
[58] Field of Search ................................ 623/19, 18, 22, 623/23

[56] References Cited

U.S. PATENT DOCUMENTS

| | | | |
|---|---|---|---|
| 4,380,090 | 4/1983 | Ramos | 3/1.912 |
| 4,718,911 | 1/1988 | Kenna | 623/22 |
| 4,801,301 | 1/1989 | Noiles | 623/23 |
| 4,969,910 | 11/1990 | Frey et al. | 623/22 |
| 5,062,853 | 11/1991 | Forte | 623/22 |
| 5,092,898 | 3/1992 | Bekki et al. | 623/22 |
| 5,507,818 | 4/1996 | McLaughlin | 623/18 |
| 5,549,697 | 8/1996 | Caldarise | 623/22 |
| 5,549,704 | 8/1996 | Sutter | 623/23 |
| 5,556,434 | 9/1996 | Epstein et al. | 623/22 |
| 5,593,445 | 1/1997 | Waits | 623/22 |
| 5,879,407 | 3/1999 | Waggener | 623/22 |

*Primary Examiner*—David J. Isabella
*Attorney, Agent, or Firm*—David L. Davis

[57] ABSTRACT

A ball-and-socket joint has a race with bearing balls interposed between the head and the socket of the joint. The race is secured to the head. In use as a prosthetic hip joint, the formation of metallic debris is reduced or completely eliminated thus eliminating or at least reducing the occurrence of the need for corrective surgery. The hip joint is of an unconstrained type which often enables correction of an accidental dislocation of the joint without surgery.

19 Claims, 4 Drawing Sheets

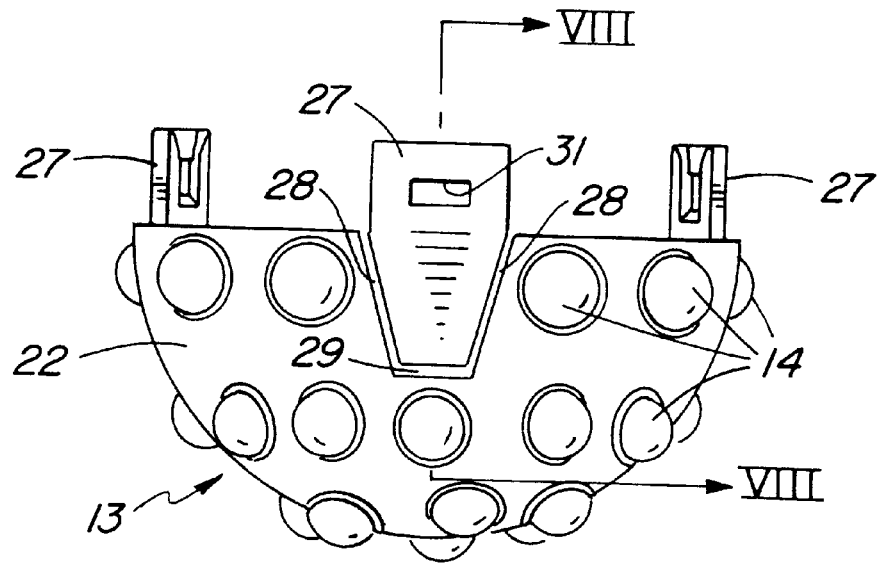
FIG. 7
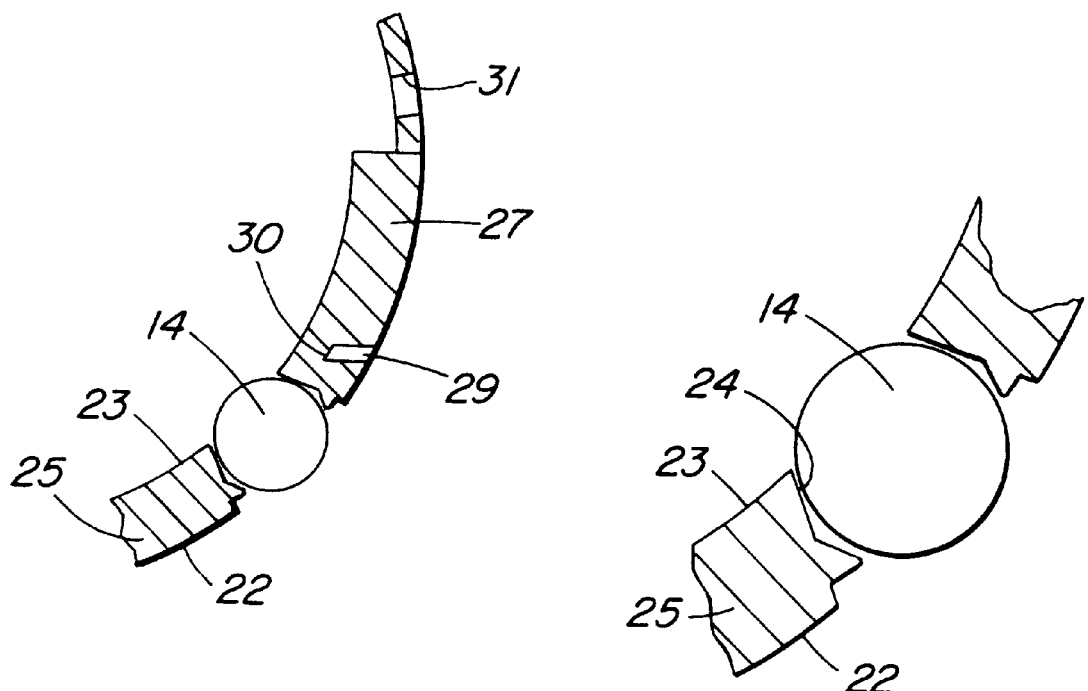
FIG. 8
FIG. 9

BALL-AND-SOCKET JOINT, PARTICULARLY A PROSTHETIC HIP JOINT

BACKGROUND OF THE INVENTION

1. Field of the Invention

The invention relates to ball-and-socket joints and in particular to prosthetic joints to be used as implanted hip joints.

2. Description of the Prior Art

Many kinds of prosthetic ball-and-socket bearings for artificial joint to be implanted in human body are known in the art. Most of the presently used joints of this type use a frictional engagement between the ball portion or head of the joint and the socket. Examples of such known joints include those described in U.S. Pat. No. 4,380,090 issued Apr. 19, 1983 (Ramos) where an artificial hip joint has a bearing insert registrable with the first cavity, and a second cavity, having an annular bearing. U.S. Pat. No. 4,801,301 issued Jan. 31, 1989 discloses a prosthetic ball-and-socket joint having a bearing member surrounding a portion of the ball portion or head and rotatable within a spherical cavity. U.S. Pat. No. 5,507,818 issued Apr. 16, 1996 (McLaughlin) discloses a multipolar endoprosthesis including multiple wedge shaped, cylindrical components for adapting the position of the head of the joint. The joint disclosed in U.S. Pat. No. 5,549,697 issued Aug. 27, 1996 (Caldarise) shows a dampening mechanism absorbing some of the loading forces communicated to the acetabular cavity. U.S. Pat. No. 5,549,704 issued Aug. 27, 1996 to Sutter is concerned with a cap forming the ball portion of the joint and its attachment to a bone without a binder.

As mentioned above, the known joints use a frictional engagement, metal-to-metal or metal-to-plastic, between the head and the socket of the joint. Failure of a conventional total hip prosthesis is most often caused by aseptic loosening of either the femoral or acetabular components. Osteolysis (loss of bone) contributes significantly to loosening. When a total hip is loose, the patient's ambulation is dramatically reduced secondary to pain. The patient must undergo revision surgery. Conventional total hip arthroplasty comprises a metal femoral head articulating with a plastic acetabular liner. Wear particles from the ultra high molecular weight polyethylene (UHMWPE) have been implicated in causing osteolysis, loosening and premature failure of total hip joints. As a result, a renewed interest exists in "metal on metal" articulations that do not contain plastic. "Metal on metal" designs have been around since the early seventies, but it is not until recently that there has been renewed scientific interest. With traditional "metal on metal" designs, a metal ball portion articulates with a spherical metal liner. This is a crude "bearing" surface that does in fact produce metallic debris. Metallic debris also contributes to inflammatory tissue responses, probable loosening and thus premature failure and the need for revision surgery.

The above disadvantages have been recognized and mentioned in U.S. Pat. No. 5,556,434 issued Sep. 17, 1996 (Epstein) wherein the three-axis movement emulating the action of a natural hip joint is provided by a universal assembly mounted on a series of roller bearings in a horizontal swivel. While this solution may reduce the formation of undesired debris, it is very complex in structure and requires special bearings having the desired strength while providing a small enough size for accommodation of the entire mechanism within the prosthetic joint structure. Even more important, the joint is inevitably of a constrained type. In other words, the dislocation of the prosthetic joint upon an accident which would merely dislocate the joint cannot occur. As a result, complicated fractures often occur at the femoral or acetabular end, or both, of the implanted joint. These require complex surgical corrections. A mere dislocation of the joint would be much more desirable.

Another known hip joint utilizing a set of bearing balls is described in U.S. Pat. No. 5,092,898 to Bekki et al. In a first group of embodiments, a complex artificial joint head portion is shown having an inner head and an outer head and a rolling ball insert therebetween. The outer surface of the outer head is polished to a mirror for engaging the acetabular roof. These embodiments, when in use, combine a limited angle movement between the inner and outer heads effected by the rolling balls. However, on more substantial angles of movement, a frictional displacement between the outer head and acetabular roof is required. In a second group of embodiments, Bekki et al show a restrained joint where the head of the joint is held in the socket by a retainer ring or assembly which is fixedly secured to the socket, i.e. to the roof of the acetabulum. Thus, any accident which might normally result in a mere dislodgement of the joint would at least destroy the retainer ring and most likely at least a part of the acetabulum, not to mention the release of the race with the rolling balls.

SUMMARY OF THE INVENTION

It is an object of the present invention to further advance the art of the joints of the above kind, which would minimize the occurrence of the debris in an implanted joint, which would be of a simple structure and at the same time would provide an unconstrained prosthetic hip joint wherein patient's own soft tissues retain the joint in operative condition and permit, in case of an accident, the excessive force tending to dislocate the joint, to result in merely a dislocation as is the case of a natural hip joint.

In general terms, the present invention provides, for use in a ball-and-socket joint, an antifriction insert adapted to be positioned between a ball portion, and a socket portion of the joint. The insert includes, in combination, a race adapted to hold a plurality of spaced apart bearing balls freely rotatable relative to the race, at a location where radially outer and radially inner portions of the bearing balls project radially outwardly and radially inwardly of the race. The radially outer and inner portions encompass a generally hemispheric major radius reference surface and a generally hemispheric minor radius reference surface, respectively. The said minor radius reference surface has a radius generally equal to that of said ball portion, while the major radius surface has a radius generally equal to that of said socket portion. Retainer means is adapted for securement to the race to retain said race in a state encompassing and secured to the ball portion of the joint at all times of use, whether in actual use or during an accidental dislocation.

The invention can also be defined, in general terms, as a kit for use in a ball-and-socket hip joint for implanting in the body. The kit comprises a generally hemispherical antifriction insert adapted to encompass a femoral head of the joint. Retainer means is included for securing the antifriction insert to the head while allowing a friction free, universal swivelling movement of the antifriction insert about the centre of the head. A generally hemispherical acetabular socket bearing of the kit is adapted to be secured to the body, directly or through an acetabular cup, and to receive said femoral head with said antifriction insert positioned between the head and the bearing. This allows a friction free swivelling motion of the head relative to the socket in a universal sense. In use, the extreme angle of the swivelling motion is limited by engagement between the retainer means and a femoral neck projecting, in an operative state of the joint, from the femoral head. The antifriction insert of the head includes a hollow, generally hemispherical race freely rotatably holding a plurality of bearing balls with radially inner sections of the bearing balls encompassing a hemispherical reference surface having a radius corresponding to that of said femoral head.

Further features and advantages of the invention will become apparent from the following detailed description of a prototype of a hip joint using elements of the present invention, with reference to the accompanying simplified, diagrammatic, not-to-scale drawings.

BRIEF DESCRIPTION OF THE DRAWINGS

FIG. 7 is a simplified side view of the race of the present invention;

FIG. 8 is a section view taken along the section line VIII—VIII in FIG. 7; and

FIG. 9 is an enlarged partial section of the race showing the arrangement of the bearing ball in the race, as shown in FIG. 8.

DETAILED DESCRIPTION OF THE PREFERRED EMBODIMENTS

Figure 1:
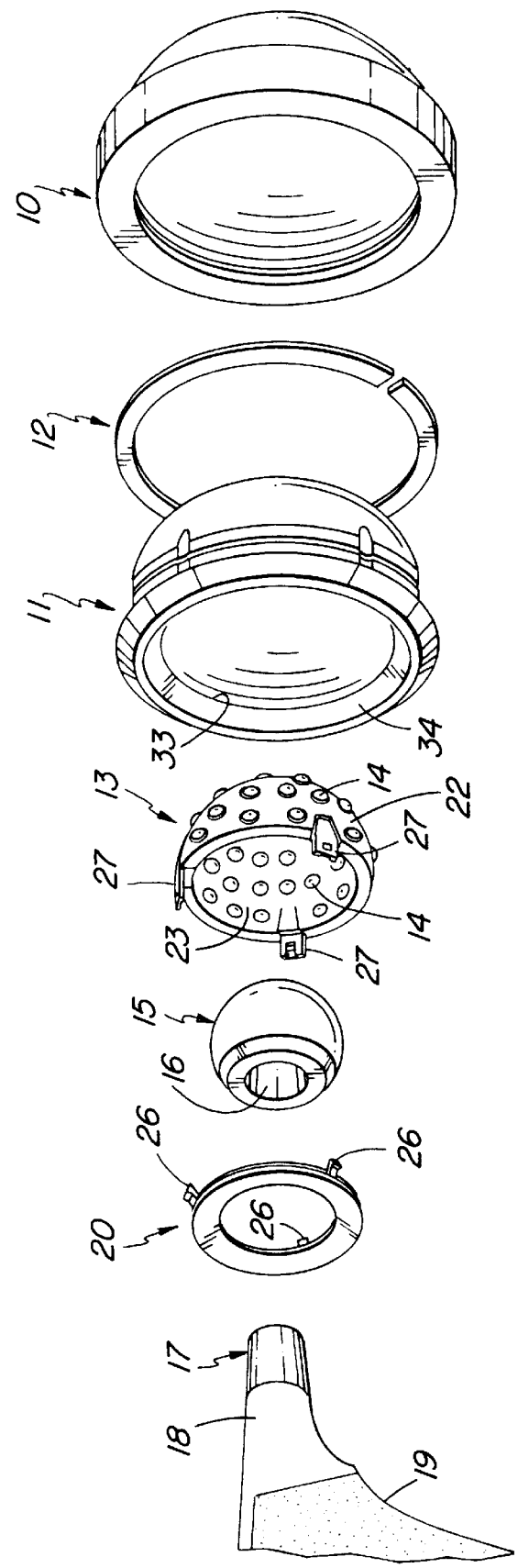
FIG. 1 is an exploded perspective view of the components of a prosthetic hip joint including the features of the present invention.

Turning firstly to FIG. 1, reference number 10 designates an acetabular shell which includes means for implanting the shell in acetabulum of a patient. Such means may comprise stems or other elements projecting from the shell 10. They are well known in the art and do not form a part of the present invention and are therefore omitted from the drawings.

Fixedly secured to the acetabular shell of a typical implanted joint is a liner 11 (also referred to as "acetabular socket bearing" which is made, in the embodiment shown, from hard stainless steel. The term "hard" in the context of the present specification and claims designates relatively high hardness of about 30 to about 65 Rockwell C. A resilient locking ring 12 serves the purpose of fixedly securing the liner 11 to the acetabular shell 10. The liner can also be made from other hard material, for instance from a ceramic composite material. Furthermore, it is also possible, even though not preferred, to provide, instead of the separate liner or socket 11, a hard lining by way of a plating of a suitably shaped cavity of the acetabular shell thus eliminating the need for a separate liner and locking ring.

A generally hemispherical race portion 13 presents an important part of the present invention. The race 13 holds a plurality of bearing balls 14 which are arranged in a compatible fashion with the cavity of the liner 11 and the surface of a ball portion or a generally spherical head 15. The head 15 has a Morse taper opening 16 which is compatible with the taper of the tip 17 of the femoral neck 18 of a femoral stem 19, the latter being adapted to be implanted in the patient's femur as is well known. The femoral neck 18 thus presents an exemplary embodiment of what is also referred to as a stem portion.

Figure 2:
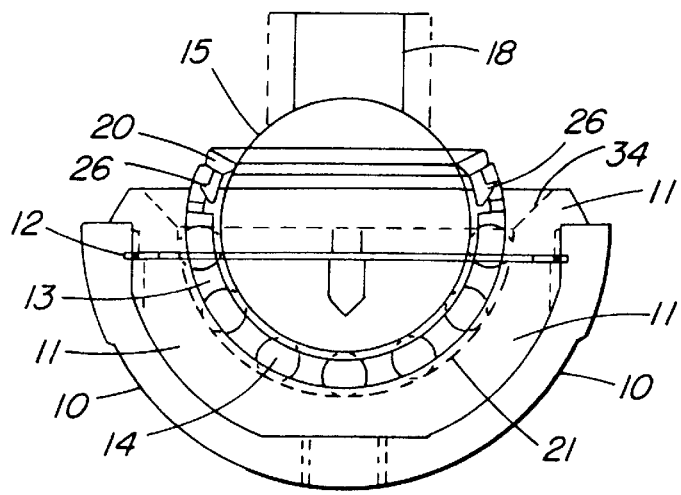
FIG. 2 is a diagrammatic representation of the implanted hip joint in a side view, showing the femoral neck of the joint in a central position.

Reference number 20 designates a retainer ring which presents an exemplary embodiment of retainer means fixely securable to the race portion 13 and movably engageable with the head as will be described. Regardless of which kind of the retainer means is provided, referring for instance to FIG. 2, it encompasses a circular locus at a location of the head, which location is (i) remote from the hemispherical race portion, (ii) remote from equatorial portion (i.e. the portion of maximum diameter) of the head, and (iii) a minimum diameter portion of the head, i.e. the portion in immediate vicinity of the stem 18. It is also shown in FIG. 2 but also in other drawings, that the combined race portion and retainer means encompass more than one-half of the head. The gist of the present invention is in the provision of an antifriction insert for use in the hip joint but also in other types of ball-and-socket joints. As is well known, a ball-and-socket joint includes a ball portion and a socket portion. In the present specification, the ball portion is also designated as head 15. The two terms, namely the "ball portion" and "head" designate the same functional element of the joint.

The antifriction insert which will now be described in detail is adapted to be positioned as a roller ball interface between the generally spherical surface of the ball portion or head 15 and a hemispherical cavity 21 of the liner 11. The surface of the head 15 defines an inner spherical reference surface having a minor radius. The cavity 21 defines an outer reference surface which has a major radius, i.e. a radius greater than the minor radius. FIGS. 2–6 shows that the outermost portions or contour of the retainer ring are disposed between the major and minor reference surfaces mentioned above. The term "antifriction" as used throughout the present specification means what is commonly used in the art of ball or roller bearings. In other words, the sliding friction between two adjacent parts is substituted by a substantially smaller rolling friction.

The antifriction insert of the present invention includes the race 13 as mentioned above. It is apparent from the drawings that the race 13 is a hollow, integrally formed, generally hemispherical cup shaped member. It has (FIGS. 5, 6) a convex exterior and a concave interior. A pattern of generally equidistantly spaced apart passages is provided in the wall 25 of the cup-shaped member. Each passage 24 is conical and tapers toward the concave interior surface 23. The bearing balls 14 are each disposed within one passage. The minor diameter of the passage 24 at the interior surface 23 is smaller than the diameter of the bearing ball 14. On the other hand, when the race 13 is being manufactured, the major diameter of each passage 24 is larger than the diameter of bearing ball 14. Generally, the diameter about midway through the passage 24 corresponds to the diameter of the bearing ball 14.

When the respective bearing ball 14 is placed into the passage 24, the major diameter end of the passage 24 is staked or otherwise deformed to reduce its cross-section at the convex exterior surface 22 to a cross-sectional area smaller than that of an equatorial area (i.e. the maximum) of the bearing ball. The size of both ends of the passage 24 and the thickness of the wall 25 are so designed that each bearing ball 14 can "float" within the passage. In other words, a small axial displacement of the bearing ball along the respective passage 14, is allowed, while a part of each bearing ball projects from both ends of the passage 24 at all times, regardless of the instant location of the bearing ball within its passage 24. This secures a free rotatable arrangement of each bearing ball 14 relative to the race 13 while the radially outer portion (at the exterior surface 22) and the radially inner portion (at the interior surface 25) of each bearing ball projects radially outwardly and radially inwardly, respectively, of the cup shaped member of the race 13.

Figure 5:
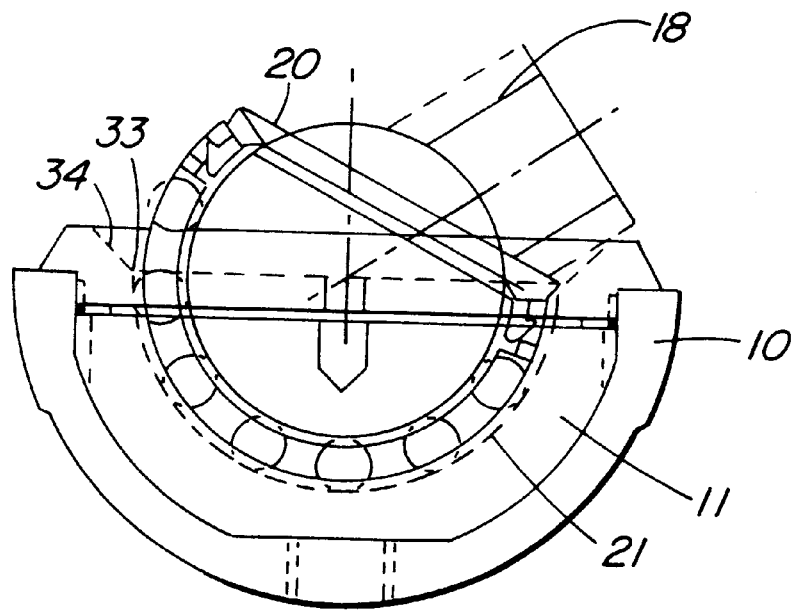
FIG. 5 is a view similar to FIG. 3 but showing the femoral neck at an extended extreme of the angular displacement which is not normally expected in operation of the joint.

FIGS. 1 and 5 also show an arrangement which is referred to as a "generally equidistant" spacing between the bearing balls 14. That is to say, the spacing need not be exactly the same in all directions and instances, but the spacing is substantially uniform over the entire hemispherical race 13.

Figure 3:
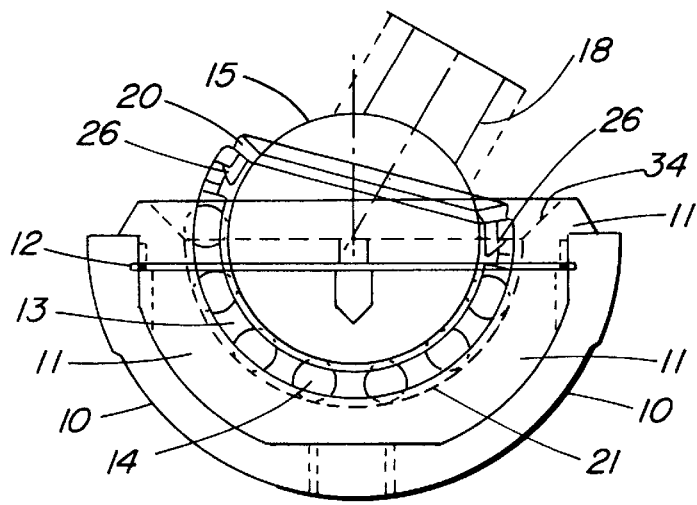
FIG. 3 is a view similar to FIG. 2 but showing the femoral neck in a first expected extreme of angular motion of the implanted joint.
Figure 4:
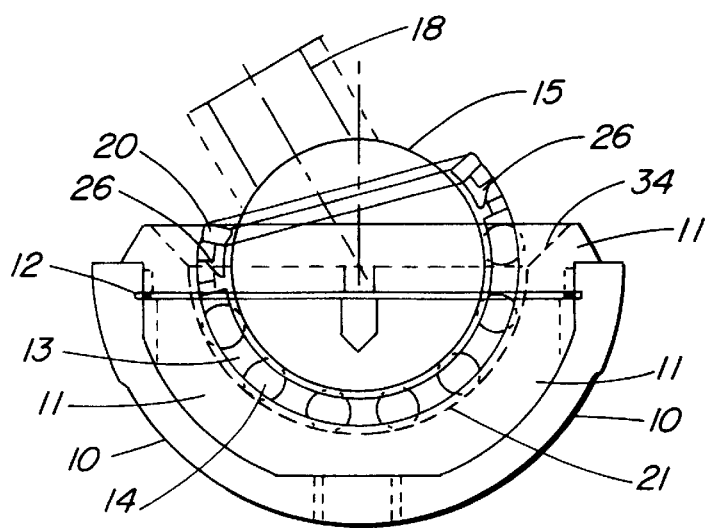
FIG. 4 is a view similar to FIG. 3 but showing the femoral neck in an opposite expected extreme angular position.

The femoral neck 18 (FIGS. 1–4) is also generally referred to as a "stem section projecting, when installed, generally radially away from the ball portion or head." The retainer ring 20 is provided with three retaining or locking hooks 26. It should be noted in this respect that the representations of FIGS. 2–4 are modified to show an embodiment which would have four retainer hooks 26, to indicate that the number of the retainer hooks is optional as long as at least two hooks are provided at a generally equidistant spacing from each other about the periphery of the ring 20, three hooks 26 being preferred.

Figure 6:
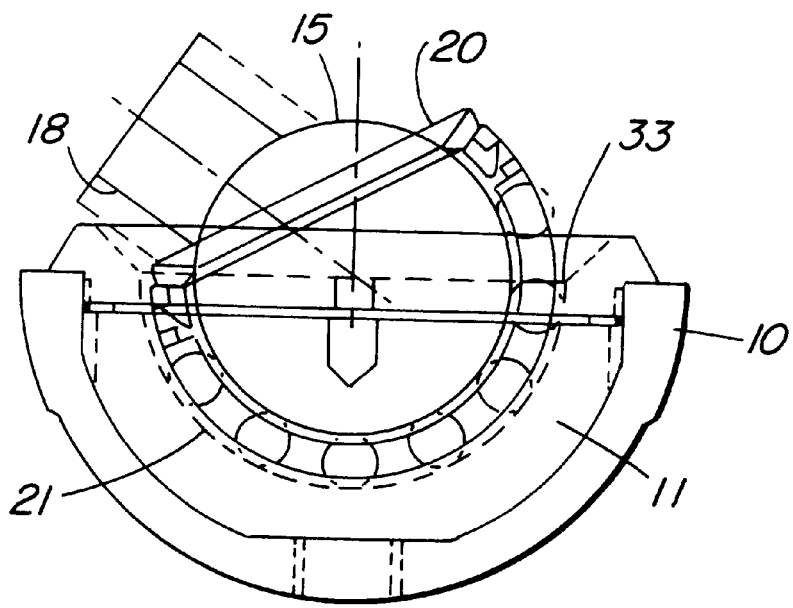
FIG. 6 is a view similar to FIG. 5 but showing the femoral neck at an opposite extended extreme of the angular displacement which is not normally expected in operation of the joint.

The hooks 26 are each adapted to engage an associated connecting member, in the embodiment shown, a resilient tab 27 which, in the embodiment shown, is integrally formed with the race 13. FIGS. 5 and 6 are illustrative of the structure of the tabs 27. FIG. 5 shows only one of the three tabs for simplicity. Each tab 27 is separated from the body of the race 13 by side slots 28, one to each side of the tab 27. The slots 28 pass all the way across the thickness of the wall 25. On the other hand, the transverse groove 29 at the root of the tab (FIG. 6) had a depth smaller than the thickness of the wall 25 to provide the required flexing of the tab 27 about the thin portion 30 at the bottom of the groove 29. The upper part of the tab 27 is thinner than the thickness of the wall 25 of the race 13 and is provided with a rectangular opening or eye 31 which is compatible with one of the hooks 26 for a releasable locking engagement therewith. The engagement between the hook 26 and the eye 31 is shown in FIGS. 2–4.

When the head is to be provided with the antifriction insert, the head, disconnected from the femoral stem, is nested in the cavity of the hemispherical race 13. The head defines more than just a hemispherical surface. A part of the head 15 with the opening 16 projects outwardly from the equatorial opening of the race 13. As best shown in FIG. 5, the tabs 27 also project above the equatorial opening of the race 13. Next, the retainer ring 20 is placed over the projecting part of the head 15 and the hooks 26 are snapped into engagement with the eyes 31. The diameter of the retaining opening of the ring 20 is smaller than that of the equatorial portion of the head. The equatorial portion, of course, presents the maximum diameter of the head 15. With the tip 17 of the femoral stem 18 impact driven into the opening 16 in the head 15, the Morse taper provides a strong, fixed securement of the femoral stem to the head 15. The race 13 with the bearing balls is now safely secured to the head 15 while permitting a rolling friction universal swivelling movement of the head 15 now encompassed by the pattern of the bearing balls 14. The angle of the universal movement between the head and the race is limited by engagement of the ring 20 with the femoral neck 18. This provides a degree of self centring of the race 13 relative to the femoral head and stem.

In practice, the acetabular cup 10 is implanted in the patient's acetabulum and the lining 11 secured to the cup 10. The femoral stem 19 (with the head 15 removed from the neck 18) is implanted in the patient's femur. The sequence of these two steps may be reversed.

In the meantime, the race 13 with the bearing balls 14 is secured to the head 15 (still removed from the femoral stem 19) by engaging the hooks 26 of the locking ring 21 with the openings 31 of the tabs 27. This results in a pre-assembly of the head with the insert 13.

The pre-assembly is subsequently attached to the femoral neck 18 and thus to the implanted femoral stem 19 by impact driving the Morse-taper tip 17 into the opening 16 in the head 15 with the resulting fixed securement of the head (now enveloped by the insert) to the patient's femur.

Eventually, the joint is reduced by inserting the head with the friction free insert into the cavity of the lining 11. The patient's own soft tissues hold the entire implanted joint in operative position.

The assembled joint provides ample angle for the desirable universal movement of the femur relative to the acetabulum. This universal motion normally takes place within the limits of the opposed external positions of the femoral neck 18 shown in FIGS. 3 and 4. It is shown that at this stage the ring 20 is approximately between the position of FIG. 2 and that of FIG. 5 (see FIG. 3) or the position of FIG. 2 and FIG. 6 (see FIG. 4). This motion normally suffices for proper function of the implanted joint. It happens only exceptionally that a an extended extreme of the angular displacement angle may be required. In such exceptional case, there are small additional movements permitted by causing the tilt of the neck 18 and of the ring 20 to positions which, theoretically, may reach the extremes indicated in FIGS. 5 and 6. In such exceptional and not normally encountered situation, the inclined ring 20 is nearly contacting the bevelled portion 34 of the liner 11. It is emphasized that this position is beyond normal operation of the joint and is beyond the expected extremes of the universal motion of the joint. Under normal circumstances, the position where the neck 18 is in the angular positions of FIGS. 3 and 4 presents the expected extremes of the angular motion of the joint.

If the joint is subjected to an accidental situation tending to dislocate the hip joint, the head 15 with the insert is dislocated from the liner 11 without subjecting the acetabular end of the joint to any stress. The retainer ring 20 holds the race with the bearing balls to the dislocated head but prevents excessive motion of the race about the head. The retainer ring combined with the femoral neck 18 secure sufficient degree of "self-centring" the race 13 on the head 15. In other words, the maximum angle of inclination of the race 13 relative to the femoral neck 18 is as shown in FIGS. 3 or 4. This is sufficient for a convenient placement of the dislocated head 15 with the race 13 back into the cavity of the liner 11. Accordingly, the correction of the dislocation by reinserting the head 15 and race 13 is done in much the same fashion as that of a natural hip joint. The replacement of the head 15 with the race 13 into the cavity of the liner 11 is facilitated by a bevelled portion 34 at the equatorial opening of the liner 11.

The strictly rolling engagement between the bearing ball, the hard head 15 and the hard liner 11, all of which are preferably of generally the same hardness within the above range results not only in a smooth motion between the femoral and acetabular sections of the joint, but—even more important—reduces the formation of metallic debris virtually to zero, thus avoiding or at least substantially reducing the need for corrective surgery of the joint.

It is known that the standard diameter of the prosthetic femoral head nowadays is 28 mm. The present invention, with the race 13 and bearing balls 14 made to fit such standard head, increases the effective diameter of the joint by twice the diameter of the bearing balls thus contributing to its better stability.

Those skilled in the art will readily appreciate that the embodiment described may be modified to a greater or lesser degree. For instance, the race 13 can be provided in a different fashion. A great variety of the securement means similar in function to the retainer ring are readily conceivable. For instance, the retainer ring could be avoided and replaced by suitably shaped split race which would encompass more than the hemispherical reference surfaces whereby the equivalent of the opening of the ring 20 would be defined by an opening in such modified race. Similarly, if a ring-shaped retainer means is preferred, there are many possibilities other than the hook-and-tab mechanism disclosed for securement of the retainer ring to the race. Accordingly, the term "retainer means" and "securement means" within the context of the present application is intended to refer not only to such means as disclosed and as used in a prototype, but to the variety of equivalent alternative devices or arrangements readily available to or conceivable by those skilled in the art. The modifications mentioned above and many other modification, therefore, fall within the scope of the present invention as defined in the accompanying claims.

I claim:

1. An antifriction insert adapted for placement over a generally spherical head of a ball-and-socket joint including a stem portion to one end of which the head is secured, to provide a rolling ball interface between the head and a cavity of a socket of the joint, said insert comprising:

(a) a generally hemispherical race portion, said race portion holding a plurality of spaced apart bearing balls freely rotatable relative to the race portion, said balls being held in the race portion such that radially outer portions and radially inner portions of the bearing balls project radially outwardly and radially inwardly of the race portion, respectively;

(b) said radially outer portions of the bearing balls being in general coincidence with a generally hemispheric, outer reference surface having a major radius;

(c) said radially inner portions of the bearing balls encompassing a generally hemispheric, inner reference surface having a minor radius;

(d) said major radius being generally equal to that of the socket of an associated joint;

(e) said minor radius being generally equal to that of the head of an associated joint; and (f) retainer means fixedly securable to said race portion and movably engageable with the head of an associated joint to encompass a circular locus at a location of the head, said locus being axially spaced from:

(i) said race portion,
        (ii) an equatorial portion of the head, and
        (iii) a minimum diameter portion of the head, the diameter of said minimum diameter portion being equal to the diameter of the head at the stem portion of an associated joint;

whereby, on securement of the retainer means to the race portion over the head of an associated joint, the combined race portion and retainer means encompass more than one-half of the head while permitting free movement in common of the combined retainer means and race portion about the head.

2. The insert of claim 1, wherein the retainer means is a retainer ring adapted to be secured to said race portion, the ring defining a retaining opening having a diameter smaller than that of the maximum diameter of an associated spherical head but larger than the diameter of said minimum diameter portion.

3. The insert of claim 1, wherein the outermost parts of the retainer means are all dimensioned to become located, upon securement to the head, between said reference surfaces, whereby the retainer means cannot engage outer edges of an associated socket thus increasing the angle of rolling friction displacement afforded by said insert.

4. The insert of claim 1, wherein:

(a) said race is a hollow, integrally formed, generally hemispherical cup shaped member having a convex exterior surface and a concave interior surface;

(b) said bearing balls are each disposed in a passage through a wall of said cup shaped member, the passage tapering toward said interior surface and defining at the interior surface an opening which is smaller in cross-section than the equatorial cross-section of the respective bearing ball;

(c) each said passage having an inwardly projecting portion reducing the cross-section of the passage at said exterior surface to a size smaller than that of the equatorial cross-section of the respective bearing ball; and (d) connecting members compatible with said retainer means to secure the race to said retainer means.

5. The insert of claim 4, wherein said cup shaped member is made from stainless steel and said inwardly projecting portion is a crimped section defining a generally circular opening.

6. The insert of claim 1, wherein (a) said race is a hollow, integrally formed, generally hemispherical cup shaped member having a convex exterior surface and a concave interior surface and defining an equatorial opening;

(b) said bearing balls are each disposed in a passage through a wall of said cup shaped member, the passage tapering toward said interior surface and defining at the interior surface an opening which is smaller in cross-section than the equatorial cross-section of the respective bearing ball; and (c) each said passage having an inwardly projecting portion reducing the cross-section of the passage at said exterior surface to a size smaller than that of the equatorial cross-section of the respective bearing ball.

(d) said cup shaped member is provided with a plurality of resilient locking tabs integrally formed with said cup-shaped member, disposed about the periphery of said equatorial opening of the cup shaped member and compatible with locking hooks projecting generally axially from said retainer ring for a locking engagement of the retainer ring with the cup shaped member.

7. A kit for producing an artifical ball-and-socket hip joint, said kit comprising:

(a) a head adapted to be sucured, or secured, to one end of a femoral portion of the hip joint, said head defining a spherical surface;

(b) a generally hemispherical, hollow, acetabular socket bearing adapted for implanting in a patient's acetabulum;

(c) a generally hemispherical race portion, said race portion holding a plurality of spaced apart bearing balls freely rotatable relative to the race portion, said balls being held in the race portion such that radially outer portions and radially inner portions of the bearing balls project radially outwardly and radially inwardly of the race portion, respectively;

(d) said radially outer portions of the bearing balls being in general coincidence with a generally hemispherical, outer reference surface having a radius generally corresponding to that of the acetabular socket bearing;

(e) said radially inner portions of the bearing balls encompassing a generally hemispheric, inner reference surface having a radius generally corresponding to that of the head; and (f) retainer means fixedly securable to said race portion and movably engageable with the head to encompass a circular locus of said spherical surface, said locus being axially spaced from:
  (i) said race portion,
  (ii) an equatorial portion of the spherical surface, and
  (iii) a minimum diameter portion of the spherical surface equal to the diameter of the head at said femoral portion;

whereby, on securement of the retainer means to the race portion over the head of an associated joint, the combined race portion and retainer means encompass more than one-half of the head while permitting free movement in common of the combined retainer means and race portion about the spherical surface.

8. The kit of claim 7, wherein the retainer means is a retainer ring adapted to be secured to said race portion, the ring defining a retaining opening having a diameter smaller than that of the maximum diameter of an associated spherical head.

9. The kit of claim 7, wherein the outermost portion of the retainer means is dimensioned to become located, upon securement of the retainer means to the head, between said reference surfaces, whereby the retainer means cannot engage outer edges of an associated inplant socket, thus increasing the angle of rolling friction displacement afforded by said insert.

10. The kit as claimed in claim 7 wherein said acetabular socket bearing has hardness generally equal to that of the bearing balls and of the head.

11. The kit of claim 10, wherein said acetabular socket bearing is a liner of an acetabular shell of an arificial hip joint.

12. The kit of claim 11 wherein said liner is made of a hard stainless steel.

13. The kit as claimed in claim 12, further comprising securement means for securing the liner to the acetabular shell of an artificial hip joint.

14. The kit of claim 7 wherein said acetabular socket bearing is made of a hard ceramic composite material.

15. The kit as claimed in claim 12, wherein the hard stainless steel has the hardness of about 30 to about 65 Rockwell C.

16. The kit of claim 7, wherein the socket bearing includes a conically outwardly flaring bevel portion surrounding an equatorial opening of said bearing, to facilitate re-inserting of an accidentally dislocated femoral head with said race into the bearing.

17. The kit of claim 7 wherein:
(a) said race is a hollow, integrally formed, generally hemispherical cup shaped member having a convex exterior surface and a concave interior surface;
(b) said bearing balls are each disposed in a passage through a wall of said cup shaped member, the passage tapering toward said interior surface and defining at the interior surface an opening which is smaller in cross-section than the equatorial cross-section of the respective bearing ball;
(c) each said passage having an inwardly projecting portion reducing the cross-section of the passage at said exterior surface to a size smaller than that of the equatorial cross-section of the respective bearing ball; and
(d) connecting members are provided compatible with said retainer means to secure the race to said retainer means.

18. The kit of claim 17, wherein said cup shaped member is made from stainless steel and said inwardly projecting portion is a crimped section defining a generally circular opening.

19. The kit of claim 7, wherein
(a) said race is a hollow, integrally formed, generally hemispherical cup shaped member having a convex exterior surface and a concave interior surface and defining an equatorial opening;
(b) said bearing balls are each disposed in a passage through a wall of said cup shaped member, the passage tapering toward said interior surface and defining at the interior surface an opening which is smaller in cross-section than the equatorial cross-section of the respective bearing ball; and
(c) each said passage having an inwardly projecting portion reducing the cross-section of the passage at said exterior surface to a size smaller than that of the equatorial cross-section of the respective bearing ball.
(d) said cup shaped member is provided with a plurality of resilient locking tabs integrally formed with said cup-shaped member, disposed about the periphery of said equatorial opening and compatible with locking hooks projecting generally axially from said retainer ring for a locking engagement of the retainer ring with the cup shaped member.

* * * * *